(12) United States Patent
Helgerson

(10) Patent No.: US 9,078,707 B2
(45) Date of Patent: Jul. 14, 2015

(54) POLYAXIAL FACET FIXATION SCREW SYSTEM WITH CANNULA INSERTER

(75) Inventor: Joel Helgerson, Erie, CO (US)

(73) Assignee: OsteoMed LLC, Addison, TX (US)

( * ) Notice: Subject to any disclaimer, the term of this patent is extended or adjusted under 35 U.S.C. 154(b) by 238 days.

(21) Appl. No.: 13/211,807

(22) Filed: Aug. 17, 2011

(65) Prior Publication Data

US 2011/0319925 A1     Dec. 29, 2011

Related U.S. Application Data

(63) Continuation-in-part of application No. 12/957,056, filed on Nov. 30, 2010, now Pat. No. 8,529,609.

(60) Provisional application No. 61/265,614, filed on Dec. 1, 2009, provisional application No. 61/374,862, filed on Aug. 18, 2010.

(51) Int. Cl.
    *A61B 17/02*     (2006.01)
    *A61B 17/70*     (2006.01)
    *A61B 1/32*     (2006.01)
    *A61B 17/34*     (2006.01)
    *A61B 17/68*     (2006.01)
    *A61B 17/86*     (2006.01)
    (Continued)

(52) U.S. Cl.
    CPC ............. *A61B 17/7064* (2013.01); *A61B 1/32* (2013.01); *A61B 17/3421* (2013.01); *A61B 17/7065* (2013.01); *A61B 17/7076* (2013.01); *A61B 17/3468* (2013.01); *A61B 17/686* (2013.01); *A61B 17/8685* (2013.01); *A61B 17/8695* (2013.01); *A61B 2017/0023* (2013.01); *A61B 2017/0046* (2013.01); *A61B 2017/00424* (2013.01); *A61B 2017/0256* (2013.01); *A61B 2017/347* (2013.01); *A61B 2017/8655* (2013.01); *A61B 2019/462* (2013.01)

(58) Field of Classification Search
    USPC ......... 600/203, 204, 208, 213, 215, 219, 226; 604/104, 164.03, 164.07, 164.1, 604/164.11, 164.12, 165.01–165.04, 604/170.02; 606/104, 86 A, 185, 190, 197, 606/916
    See application file for complete search history.

(56) References Cited

U.S. PATENT DOCUMENTS

| | | |
|---|---|---|
| 324,768 A | 8/1885 | Hunt |
| 958,127 A | 5/1910 | Hovrud |
| 1,155,844 A | 10/1915 | Smith |

(Continued)

FOREIGN PATENT DOCUMENTS

| | | |
|---|---|---|
| EP | 0932367 B1 | 11/2003 |
| WO | WO2004019757 | 3/2004 |

(Continued)

*Primary Examiner* — Michael T Schaper
(74) *Attorney, Agent, or Firm* — Norton Rose Fulbright US LLP

(57) ABSTRACT

A screw system includes a screw and a washer assembly captive to the screw. The washer assembly is polyaxially pivotable relative to the screw. The screw may be freely rotated in one direction relative to the washer assembly, but frictionally binds with the washer assembly when rotated in a second direction. A cannula insertion system includes an instrument and a cannula. The instrument may include a dilator. The cannula insertion system may have a locked setting in which the dilator is fixed relative to the cannula, and an unlocked setting in which the dilator is slidable relative to the cannula. A surgical method uses the cannula insertion system to implant the screw system.

5 Claims, 26 Drawing Sheets

(51) Int. Cl.
  *A61B 17/00* (2006.01)
  *A61B 19/00* (2006.01)

(56) References Cited

U.S. PATENT DOCUMENTS

| | | | |
|---|---|---|---|
| 1,391,186 A | | 9/1921 | Hill |
| 1,428,111 A | | 9/1922 | Molesworth |
| 1,609,645 A | | 12/1926 | DeWire |
| 1,627,404 A | | 5/1927 | Marcel |
| 1,792,381 A | | 2/1931 | Paul |
| 2,583,896 A | | 1/1952 | Siebrandt |
| 2,769,441 A | * | 11/1956 | Abramson ............... 600/184 |
| 3,181,584 A | | 5/1965 | Borowsky |
| 3,865,307 A | | 2/1975 | Schiro |
| 4,290,328 A | | 9/1981 | Clark |
| 5,125,489 A | | 6/1992 | Cha |
| 5,261,909 A | | 11/1993 | Sutterlin |
| 5,478,342 A | | 12/1995 | Kohrs |
| 5,527,312 A | | 6/1996 | Ray |
| 5,556,411 A | * | 9/1996 | Taoda et al. ............... 606/185 |
| 5,611,800 A | | 3/1997 | Davis |
| 5,893,889 A | | 4/1999 | Harrington |
| 5,908,431 A | * | 6/1999 | Battenfield ............... 606/167 |
| 6,148,696 A | | 11/2000 | Chiang |
| 6,227,782 B1 | | 5/2001 | Bowling et al. |
| 6,248,108 B1 | | 6/2001 | Tormala et al. |
| 6,443,987 B1 | | 9/2002 | Bryan |
| 6,485,518 B1 | | 11/2002 | Cornwall |
| 6,502,679 B1 | | 1/2003 | Wang |
| 6,565,573 B1 | | 5/2003 | Ferrante |
| 7,060,068 B2 | | 6/2006 | Tromanhauser |
| 7,261,506 B2 | | 8/2007 | Smolarek |
| 7,294,128 B2 | | 11/2007 | Alleyne |
| 7,396,360 B2 | | 7/2008 | Lieberman |
| 7,522,953 B2 | | 4/2009 | Kaula |
| 7,563,275 B2 | | 7/2009 | Falahee |
| 7,575,343 B2 | | 8/2009 | Li |
| 7,708,761 B2 | | 5/2010 | Petersen |
| 7,824,429 B2 | | 11/2010 | Culbert |
| 8,128,666 B2 | | 3/2012 | Falahee |
| 8,162,942 B2 | | 4/2012 | Coati |
| 2003/0032960 A1 | | 2/2003 | Dudasik |
| 2005/0077688 A1 | * | 4/2005 | Voegele et al. ............... 277/628 |
| 2005/0228386 A1 | | 10/2005 | Ziolo et al. |
| 2006/0074425 A1 | | 4/2006 | Sutterlin |
| 2006/0111779 A1 | | 5/2006 | Petersen |
| 2006/0217713 A1 | | 9/2006 | Serhan et al. |
| 2006/0217715 A1 | | 9/2006 | Serhan et al. |
| 2006/0235391 A1 | | 10/2006 | Sutterlin |
| 2006/0287583 A1 | * | 12/2006 | Mangiardi ............... 600/208 |
| 2008/0021480 A1 | | 1/2008 | Chin |
| 2008/0147079 A1 | | 6/2008 | Chin |
| 2008/0255622 A1 | | 10/2008 | Mickiewicz |
| 2009/0054903 A1 | | 2/2009 | Falahee |
| 2009/0076551 A1 | | 3/2009 | Petersen |
| 2009/0099602 A1 | | 4/2009 | Aflatoon |
| 2009/0192551 A1 | | 7/2009 | Cianfrani |
| 2009/0234397 A1 | | 9/2009 | Petersen |
| 2009/0312798 A1 | | 12/2009 | Varela |
| 2009/0312800 A1 | | 12/2009 | Chin |
| 2010/0174324 A1 | | 7/2010 | Derouet |
| 2010/0222829 A1 | | 9/2010 | Petersen |
| 2011/0087169 A1 | * | 4/2011 | Parihar et al. ............ 604/167.03 |

FOREIGN PATENT DOCUMENTS

| | | |
|---|---|---|
| WO | WO2006017507 | 2/2006 |
| WO | WO2006057943 | 6/2006 |
| WO | WO-2007/070819 A2 | 6/2007 |
| WO | WO2007084900 | 7/2007 |
| WO | WO2007109402 | 9/2007 |
| WO | WO2007120903 | 10/2007 |
| WO | WO2007127610 | 11/2007 |
| WO | WO2007127687 | 11/2007 |
| WO | WO2007143709 | 12/2007 |
| WO | WO2008086533 | 7/2008 |
| WO | WO2008106240 | 9/2008 |
| WO | WO2008127415 | 10/2008 |
| WO | WO2008127978 | 10/2008 |
| WO | WO2008153732 | 12/2008 |
| WO | WO2009006622 | 1/2009 |
| WO | WO2009067486 | 5/2009 |
| WO | WO2009134888 | 11/2009 |
| WO | WO-20091134896 A2 | 11/2009 |
| WO | WO-2010/036864 A1 | 4/2010 |

* cited by examiner

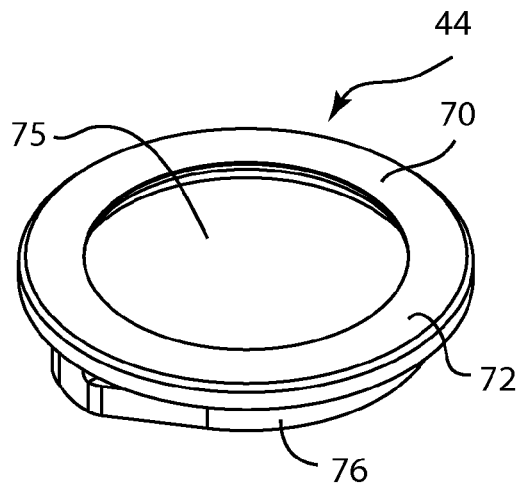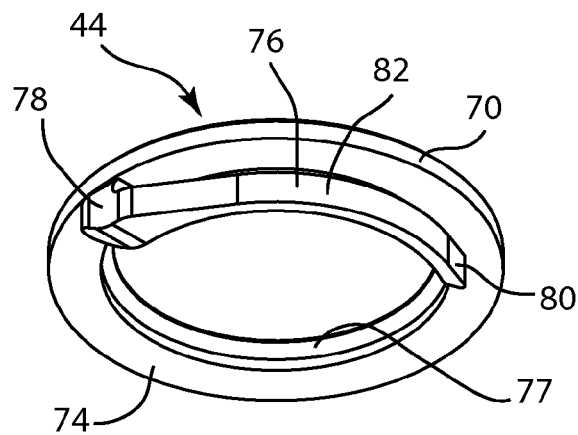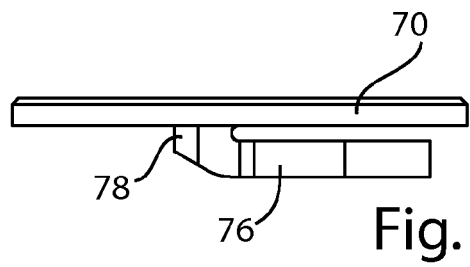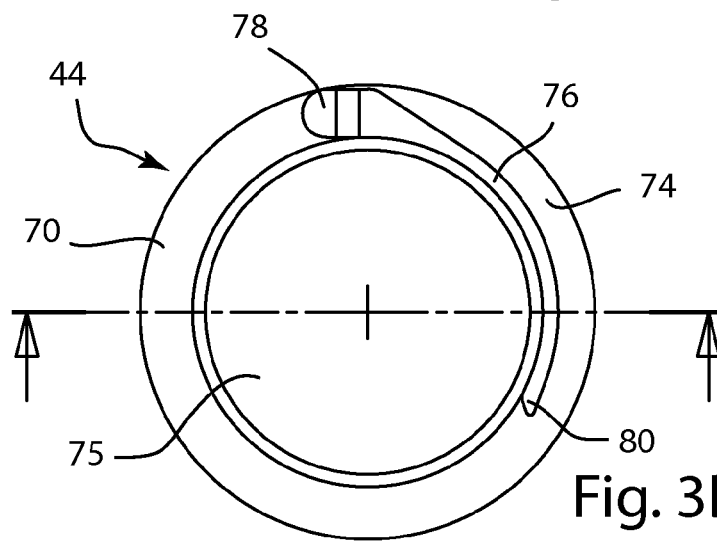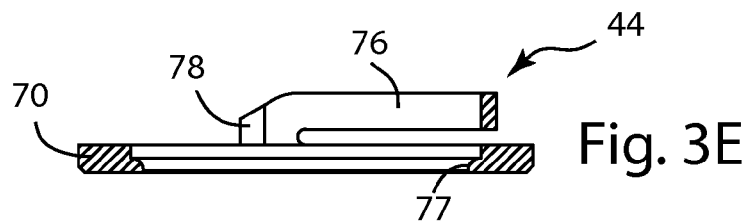

POLYAXIAL FACET FIXATION SCREW SYSTEM WITH CANNULA INSERTER

CROSS-REFERENCE TO RELATED APPLICATIONS

This application is a continuation-in-part of:

pending prior U.S. patent application Ser. No. 12/957,056 filed 30 Nov. 2010, and is entitled "POLYAXIAL FACET FIXATION SCREW SYSTEM".

U.S. patent application Ser. No. 12/957,056 claims the benefit of:

expired prior U.S. Provisional Patent Application No. 61/265,614 filed 1 Dec. 2009, and is entitled "ANTI-BACK OUT POLYAXIAL FACET FIXATION SCREW SYSTEM"; and pending prior U.S. Provisional Patent Application No. 61/374,862 filed 18 Aug. 2010, and is entitled "CANNULA INSERTER".

The above-identified documents are incorporated herein by reference.

BACKGROUND

1. Technical Field

The present disclosure relates to orthopedic screw systems for bone fixation, and more particularly, to providing facet joint fixation screw systems with anti-backout features which prevent unintentional withdrawal of the screw and instrument systems to facilitate minimally invasive screw placement.

2. The Relevant Technology

Loosening is a commonly encountered problem with screw fixation. A screw may work its way loose over time, such that fixation is compromised or the screw head protrudes to an undesirable extent from the surrounding material. Loosening is seen in orthopedic applications, such as facet joint fixation or facet joint fusion, at least partially because normal physiologic movement tends to encourage screw migration, and the bone into which the screw is driven tends to remodel over time. The three-dimensional topography of the bone surface presents an additional challenge in achieving secure fixation. The present disclosure provides a low-profile, self-contained, polyaxial, one-way screw and washer system that automatically and continuously resists any tendency of the screw to unthread from the surrounding material.

Bone screws may be inserted with a minimally invasive surgical technique. An example of a minimally invasive surgical technique is one in which the surgical exposure is minimized. Bone screws may be inserted through a surgical exposure which forms a passageway between the skin incision and a target location on a bone. The passageway may be oriented along a final implantation trajectory of the screw, i.e., along a center longitudinal axis of the screw. The width of the passageway may be only slightly greater than the outer dimension of the screw, a corresponding screwdriver, or other system component. The passageway may be held open by a tube or cannula. The cannula may also protect surrounding tissues from collateral damage during the surgical procedure of inserting the screw. The present disclosure provides a cannula insertion system for forming a passageway and holding the passageway open during the surgical procedure.

BRIEF DESCRIPTION OF THE DRAWINGS

Various embodiments will now be discussed with reference to the appended drawings. It is appreciated that these drawings depict only typical embodiments of the disclosed subject matter and are therefore not to be considered limiting of the scope.

FIG. 3A illustrates a top perspective view of a cap of the washer assembly of FIG. 1A; FIG. 3B illustrates a bottom perspective view of the cap of FIG. 3A; FIG. 3C illustrates a side view of the cap of FIG. 3A; FIG. 3D illustrates a bottom view of the cap of FIG. 3A; FIG. 3E illustrates a side cross-sectional view of the cap of FIG. 3A;

DETAILED DESCRIPTION OF THE PREFERRED EMBODIMENTS

The present disclosure relates to systems and methods used in orthopedic surgery, and in particular, to facet joint fixation. Those of skill in the art will recognize that the systems and methods described herein may be readily adapted for other bone or joint fixation procedures. Those of skill in the art will also recognize that the following description is merely illustrative of the principles of the technology, which may be applied in various ways to provide many different alternative embodiments. This description is made for the purpose of illustrating the general principles of this technology and is not meant to limit the inventive concepts in the appended claims.

Figure 1A:
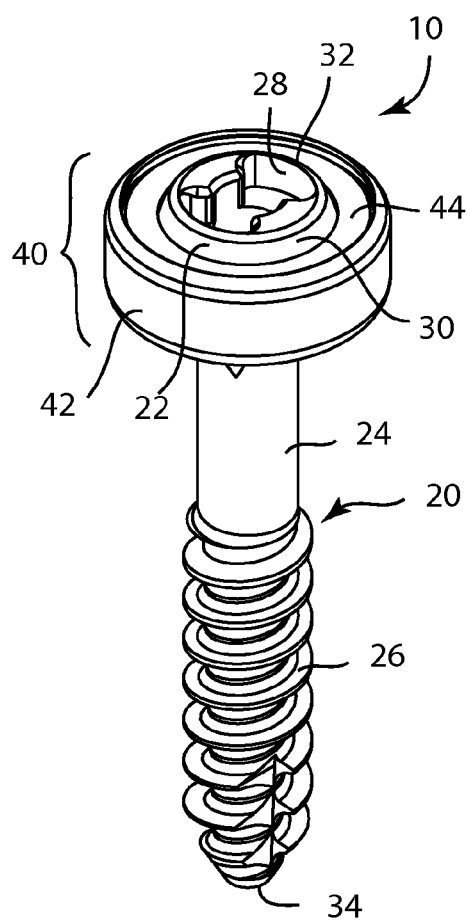
FIG. 1A illustrates a top perspective view of a system including a screw and a washer assembly.
Figure 1B:
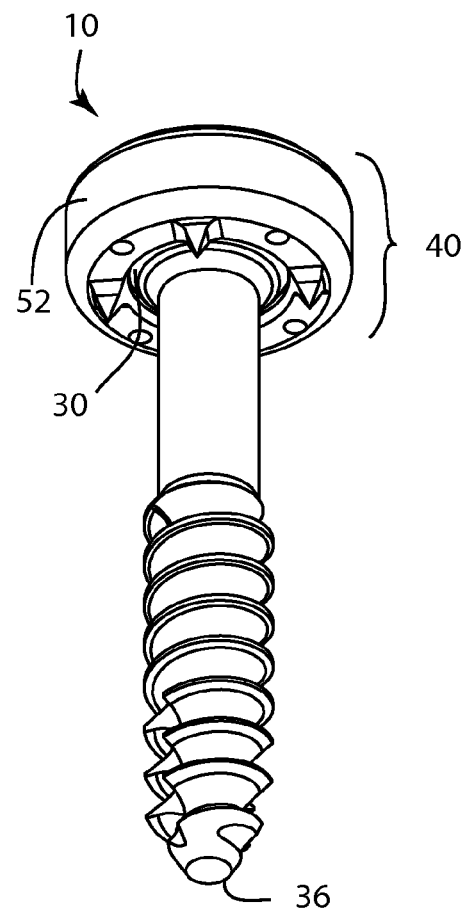
FIG. 1B is a bottom perspective view of the system of FIG. 1A.

Referring to FIGS. 1A and 1B, top and bottom perspective views illustrate a facet fixation screw system 10, comprising a screw 20 and a washer assembly 40. The washer assembly is captive to the head of the screw. The washer assembly includes an anti-backout mechanism which allows the screw to be freely rotated in one direction relative to the washer assembly, but binds the screw to the washer assembly when the screw is rotated in the opposite direction.

Screw 20 includes a spherical head 22 and a shaft 24. The shaft 24 includes a threaded portion 26 extending along a portion of the shaft. The entire length of the shaft may be threaded, or some portion or portions thereof. The thread pitch may be constant along the threaded portion, or may vary. Preferably, the shaft 24 includes a cannulation 25 to allow placement of the screw over a guide wire, but non-cannulated embodiments may also be provided. A drive feature 28 on the head 22 is shaped to cooperate with a driver instrument to facilitate placement, polyaxial adjustment and/or rotational driving of the screw. In the embodiment shown, the drive feature has a dogbone or bowtie shape; however other drive feature shapes are possible, including but not limited to: hexagon, pentagon, square, triangular, rectangular, cross, star, or other driver shapes known in the art. The drive feature 28 may be a recess as shown; in other embodiments the drive feature 28 may protrude to cooperate with a driver instrument having a complementary recessed driving feature. The head 22 further includes a spherical bearing surface 30. The screw 20 further includes a first end 32 which may be a proximal end, and at which the head 22 is located; and a second end 34 which may be a distal end, and at which a tip 36 of the shaft 24 is located.

Figure 4A:
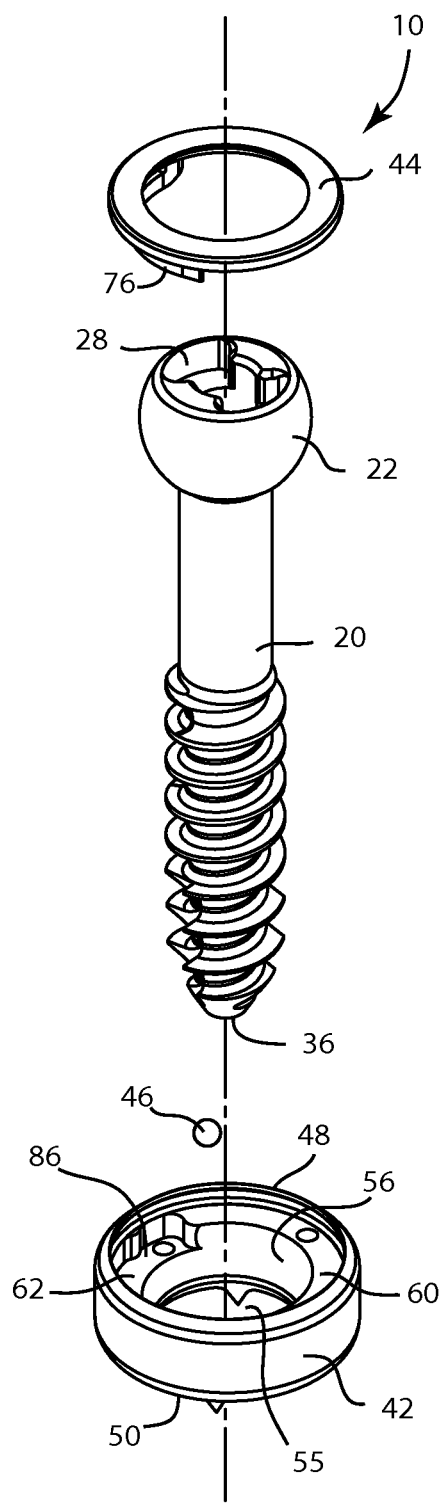
FIG. 4A illustrates a top perspective exploded view of the system of FIG. 1A.
Figure 4B:
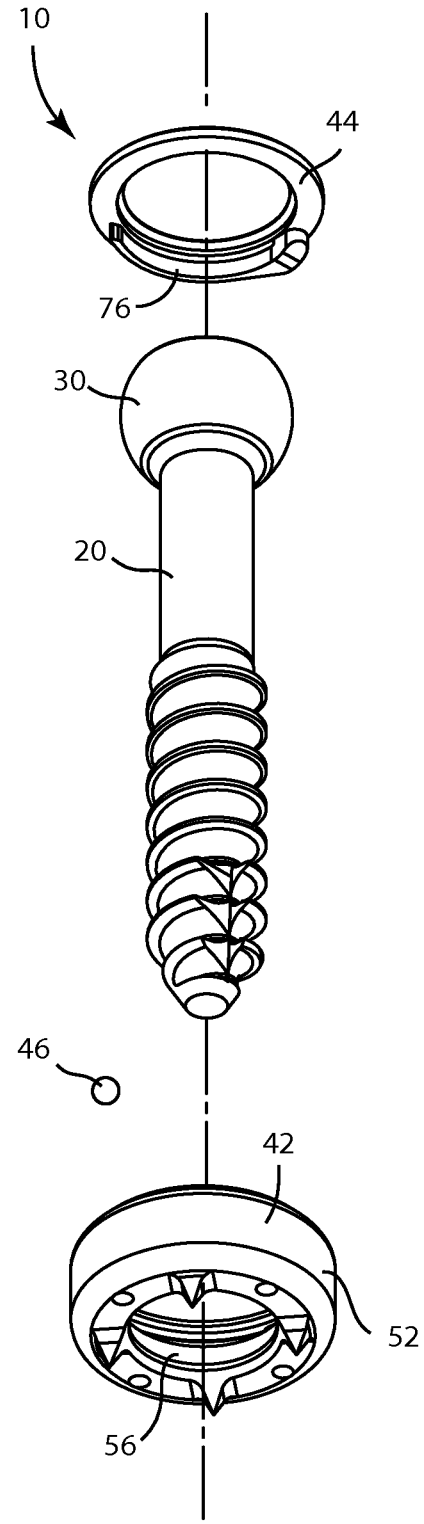
FIG. 4B illustrates a bottom perspective exploded view of the system of FIG. 1A.

Washer assembly 40 includes a washer 42 and cap 44. The washer assembly may further include a ball 46 (as best seen in FIGS. 4A and 4B) which is captured between the washer 42, the cap 44, and the head 22 when the washer assembly is operatively assembled with the screw 20 as in FIGS. 1A and 1B. The system 10 may be operatively assembled during manufacture and provided to the end users in the operatively assembled form, in sterile packaging.

Figure 2A:
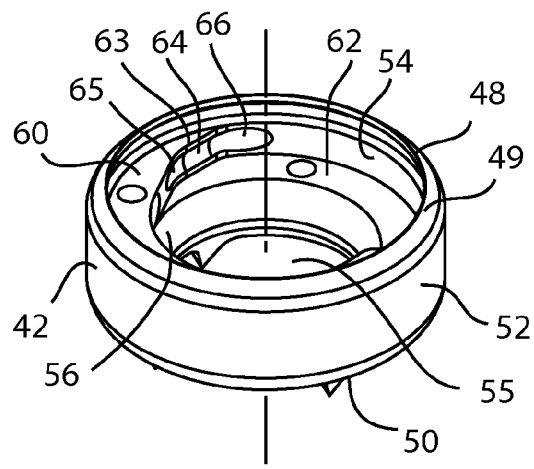
FIG. 2A illustrates a top perspective view of a washer of the washer assembly of FIG. 1A.
Figure 2B:
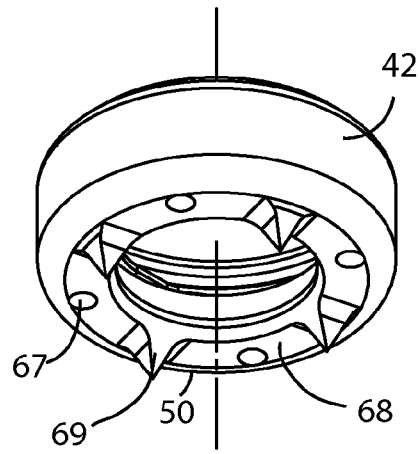
FIG. 2B illustrates a bottom perspective view of the washer of FIG. 2A.
Figure 2C:
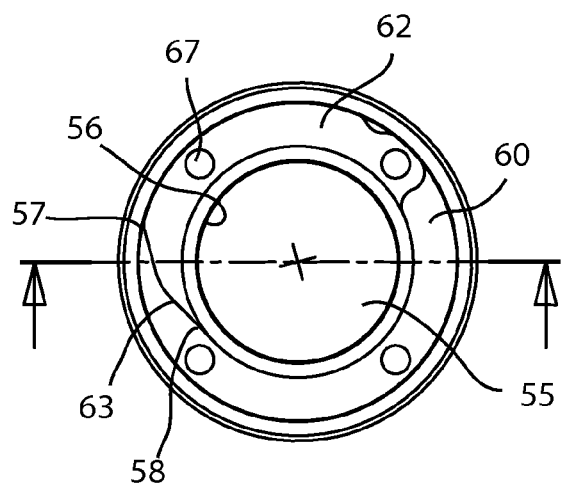
FIG. 2C illustrates a top view of the washer of FIG. 2A.
Figure 2D:
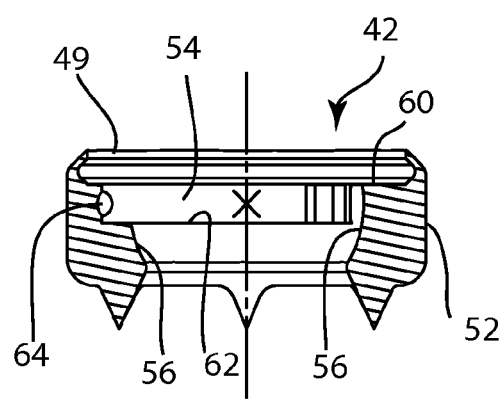
FIG. 2D illustrates a side cross-sectional view of the washer of FIG. 2A.

FIGS. 2A-2D show washer 42 in more detail. Washer 42 is annular, and has a first end 48 and a second end 50. First end 48 terminates with a relatively thin annular lip 49 which may project slightly toward the center of the washer 42. An outer peripheral wall 52 extends exteriorly between the first end 48 and the second end 50. An inner surface 54 extends interiorly between the first end 48 and the second end 50, forming a boundary to an aperture 55. An annular spherical recess 56 occupies a portion of the inner surface 54, and may form a socket to receive screw head 22. A portion of the annular spherical recess 56 is bounded toward the first end 48 by a first shelf 60, and the remainder is bounded toward the first end by a second shelf 62, which is recessed from, and may be described as lower than, the first shelf 60. Between the first shelf 60 and the second shelf 62, a portion of the inner surface 54 forms a ramp 63. The ramp 63 extends partially around the socket, or spherical recess 56, between a first end 57 which is outwardly displaced from the socket and a second end 58 which is tangential to the socket. An alcove 64 having a partial circular cross section is recessed into the inner surface 54; at least a portion of the alcove 64 overlaps the ramp 63, as seen in FIGS. 2A and 2D. Alcove 64 includes a first shallow portion 65 and a second deep portion 66, the depth of the alcove and the distance of the alcove from the spherical recess 56 increasing between the first and second portions. In this embodiment, alcove 64 has a cross section comprising an arc of a circle with a diameter which is complementary to the outer diameter of ball 46. The diameter of the circle may be slightly less than the outer diameter of ball 46, so that ball 46 is supported on the edges of alcove 64. Alcove 64 may be further described as a semicircular dished face, or a groove.

At least one bore 67 may extend longitudinally through the washer between the first end 48 and the second end 50, and may, for example, provide access for cleaning during or after manufacturing. The second end 50 of the washer 42 includes a bone engagement surface 68, at least a portion of which may be compressed against bone material when the screw system is implanted. At least one spike 69 protrudes from the second end 50. The spikes 69 may penetrate bone to provide additional fixation and/or rotation prevention. In other embodiments, pegs, nails, pins, keels or other bone-penetrating features may be included in place of or in addition to spikes 69, or no bone-penetrating features may be included. The bone engagement surface 68 may be roughened or porous to promote bone ongrowth or ingrowth; bone growth or other therapeutic agents may also be provided on the bone engagement surface 68.

Referring to FIGS. 3A-3E, the cap 44 includes a ring 70, the ring having a first side 72 and a second side 74 with an aperture 75 extending through the ring between the first and second sides 72, 74. A beam 76, which may be a cantilever beam, projects from the second side 74. A fixed end 78 of the beam is fixed to the ring, and a free end 80 is adjacent, but unconnected to, the ring 70. A beam body 82 extends between the fixed end 78 and the free end 80, is curved to follow the curvature of the ring 70, and may be parallel to the ring 70. The beam 76 may have the same radius of curvature as the ring 70, so that it extends along and overlaps a portion of the ring 70. The aperture 75 may include a lip 77 which has a diameter smaller than the equatorial diameter of the screw head 22.

Figure 5B:
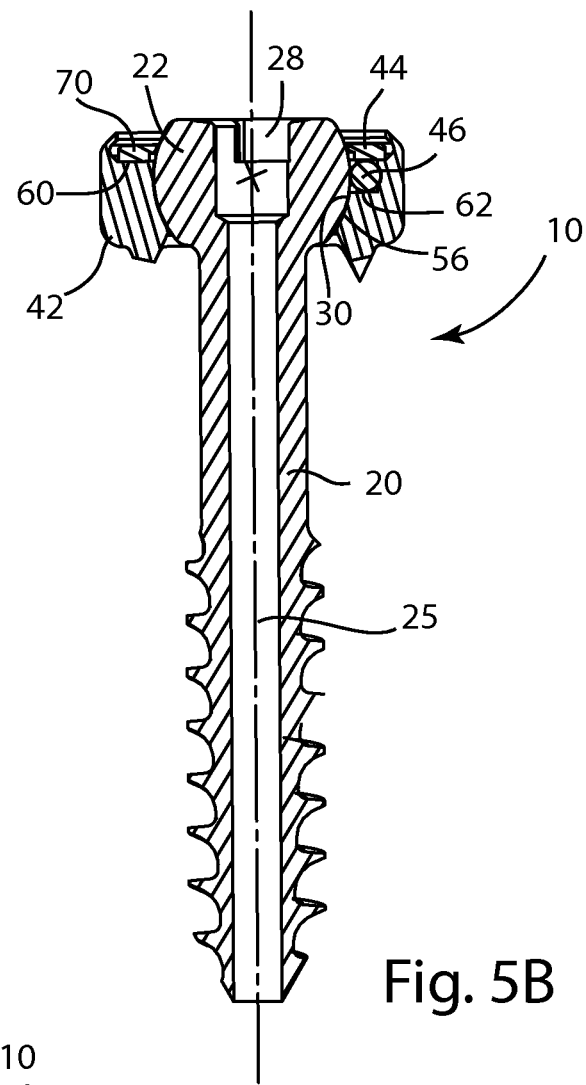
FIG. 5B illustrates a longitudinal cross-sectional view of the system of FIG. 5A.
Figure 5A:
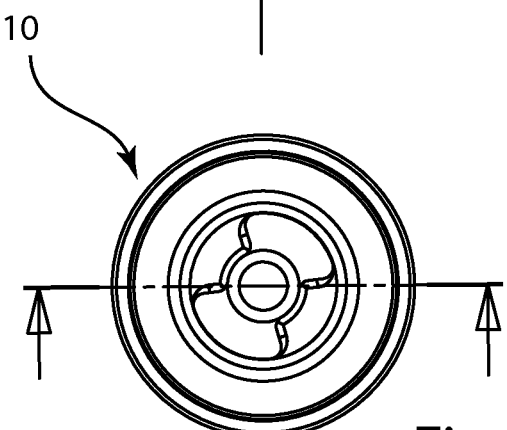
FIG. 5A illustrates a top view of the system of FIG. 1A.
Figure 6:
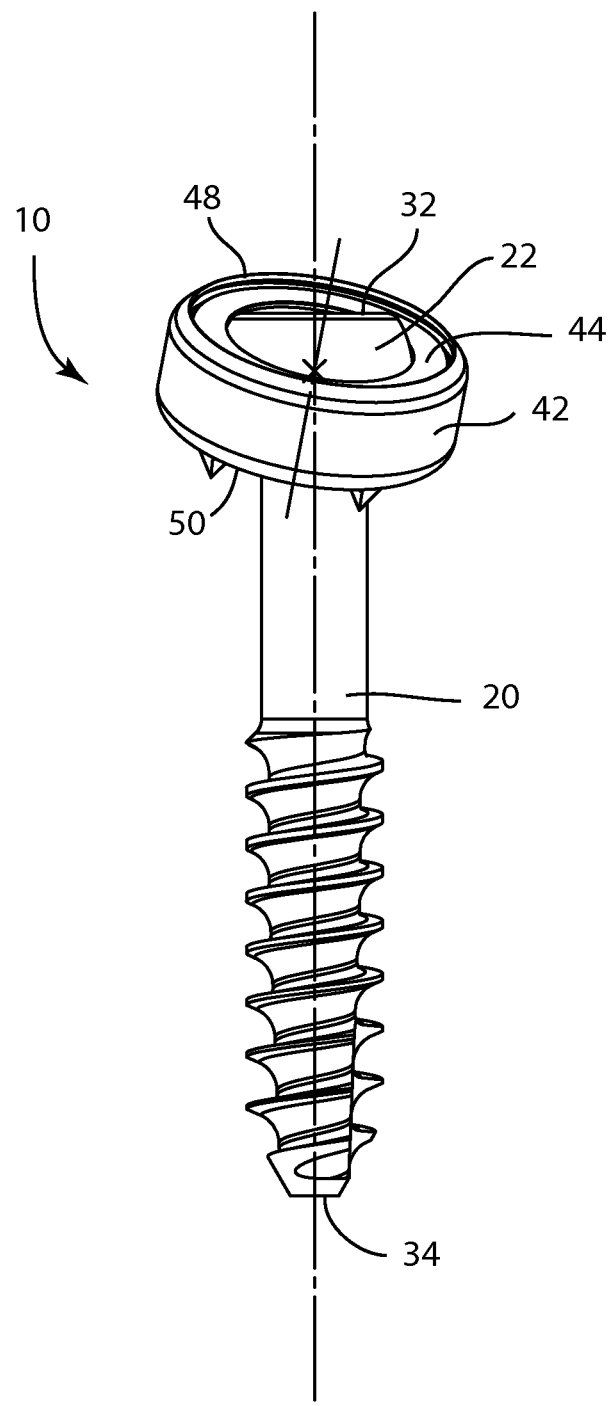
FIG. 6 illustrates a top perspective view of the system of FIG. 1A, showing the washer assembly polyaxially pivoted relative to the screw.
Figure 7A:
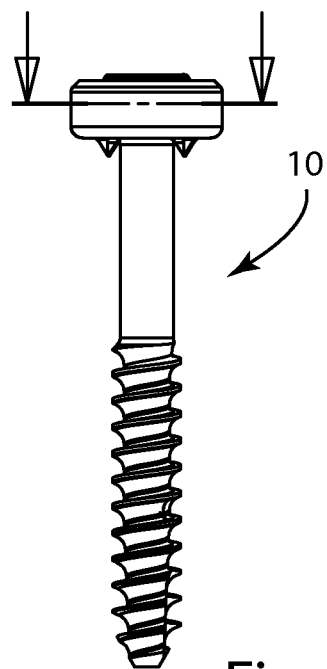
FIG. 7A illustrates a side view of the system of FIG. 1A.
Figure 7B:
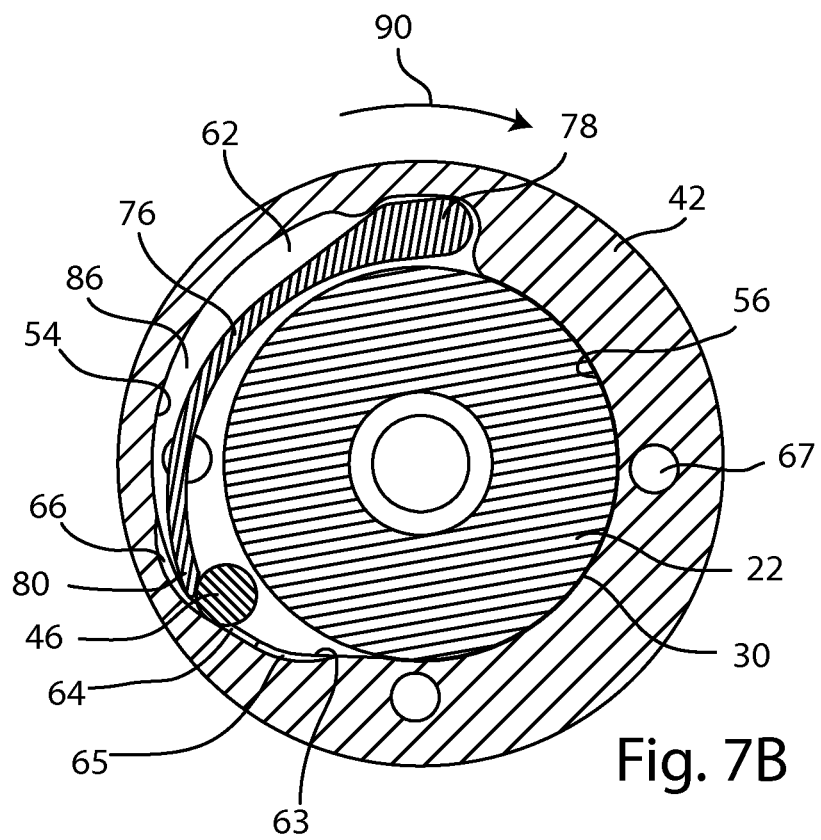
FIG. 7B illustrates a top cross-sectional view of the system of FIG. 7A with the system in an unlocked configuration in which the screw can rotate freely in a first direction relative to the washer assembly.
Figure 8A:
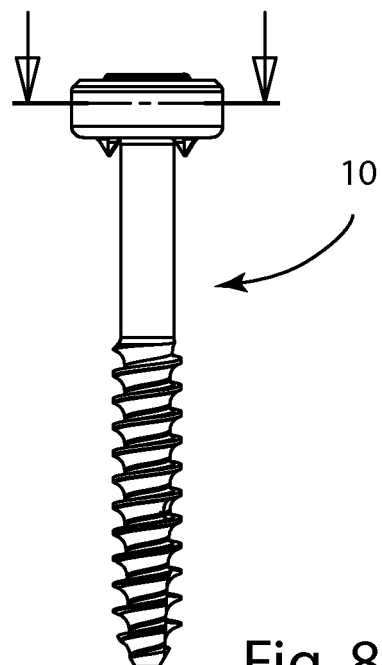
FIG. 8A illustrates a side view of the system of FIG. 1A.
Figure 8B:
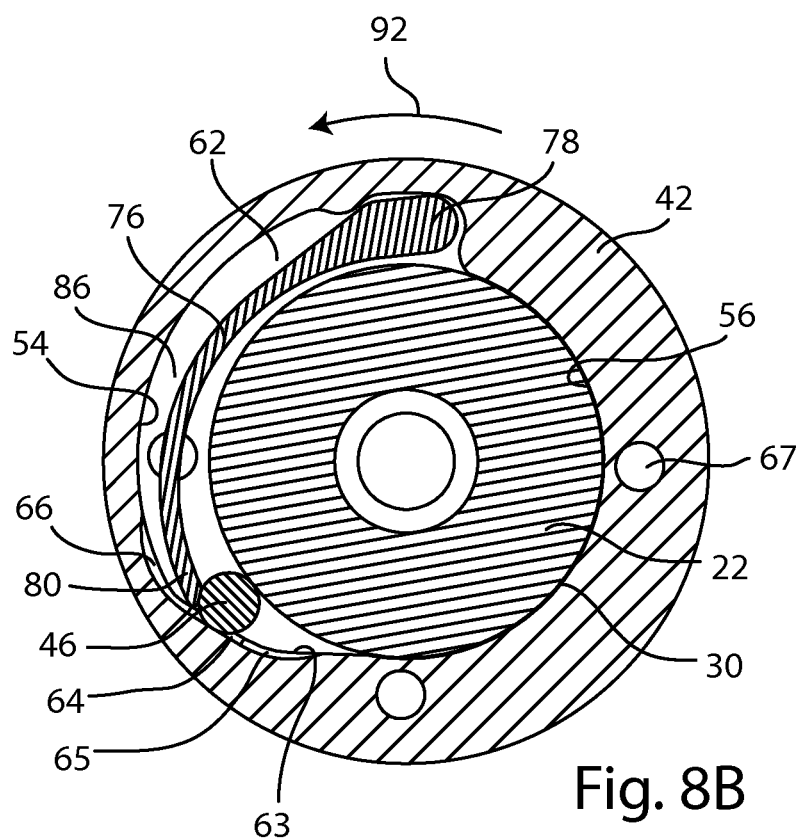
FIG. 8B illustrates a top cross-sectional view of the system of FIG. 8A with the system in a locked configuration in which the screw and washer assembly are frictionally locked together so that the screw is unable to rotate freely in a second direction relative to the washer assembly.

FIGS. 4A-4B depict screw system 10 in exploded views, and FIG. 5B is a cross-sectional view of the system in an operatively assembled configuration. When system 10 is assembled, screw 20 is received through washer 42, with tip 36 oriented in the same general direction as second end 50, and head 22 toward first end 48. Screw head 22 is retained by washer 42, with spherical bearing surface 30 bearing against annular spherical recess 56. Head 22 and washer 42 may thus form a ball and socket joint, with head 22 polyaxially pivotable relative to washer 42, as seen best in FIG. 6. Ball 46 is positioned inside washer 42 on second shelf 62, between head 22 and alcove 46. Cap 44 is positioned on washer 42, with a portion of ring 70 resting on first shelf 60. As best seen in FIGS. 7B and 8B, beam 76 extends from the second side 74 of the cap and is received in a gap 86 formed between head 22, second shelf 42, and inner surface 54 of washer 42. Free end 80 of beam 76 is adjacent alcove 64 of the washer, and ball 46 is between free end 80 and head 22. The free end 80 continuously spring biases the ball 46 toward the second end of the ramp 63. In other embodiments, ball 46 may be biased toward the second end of the ramp 63 by another kind of known spring, such as a spring clip, retaining ring, compression spring, extension spring, leaf spring, or torsion spring. In additional embodiments, ball 46 may be biased toward the second end of the ramp 63 by other known biasing means, such as magnetic bias, gravitational bias, or shape memory bias. Cap 44 is secured to washer 42 through a press-fit connection; as cap is pressed onto washer 42 in the described position, lip 49 of the washer may be deformed. In other embodiments, cap 44 may be secured to washer 42 by laser welding, a snap fit, a taper fit, a friction fit, threads, or any other known suitable connection means. It is appreciated that head 22 is polyaxially pivotable relative to washer 42 both before and after cap 44 is attached to washer 42.

Referring to FIGS. 7B and 8B, when screw system 10 is operatively assembled, screw 20 can rotate freely relative to washer assembly 40 in a first direction, but becomes rigidly locked to washer assembly 40 when rotated in a second direction. As shown in FIG. 7B, head 22 may be freely rotated in a first direction 90, which may be clockwise. As head 22 rotates, ball 46 is urged along alcove 64 in ramp 63, from shallow portion 65 toward deep portion 66. As ball 46 encounters free end 80 of beam 76, the beam is deflected toward deep portion 66, and the spring bias of the beam is temporarily overcome, allowing free rotation of the head 22. Although in FIG. 7B a small gap is shown between ball 46 and head 22, it is appreciated that ball 46 and head 22 may be in slight contact, yet head 22 is still able to freely rotate relative to washer 42.

As shown in FIG. 8B, rotation of head 22 in a second direction 92, which may be counterclockwise and opposite the first direction, causes a frictional lock to form between head 22 and washer assembly 40. As head 22 is rotated in the second direction 92, ball 46 is urged along alcove 64 in ramp 63 toward shallow end 65. Ball 46 is further urged toward shallow end 65 by the spring bias of beam 76. Ball 46 becomes jammed or wedged between alcove 64 and head 22, and may be deformed against head 22 as a result of the wedging action. In the present embodiment, ball 46 becomes wedged between two points of contact along the edges of alcove 64 and a single point of contact with head 22; the single point of contact may transform into a contact patch or area due to deformation of the ball 46 against the head 22. Further rotation of head 22 in the second direction is prevented; however washer 42 may still be polyaxially pivotable relative to head 22.

FIGS. 9-26 illustrate a cannula insertion instrument 100 and cannula 130, which may be components of a cannula insertion system. The cannula insertion instrument may also be referred to as a cannula inserter 100. The cannula inserter may releasably couple to the cannula, dilate a path through soft tissue, insert the cannula into or through the tissue, and uncouple from the cannula to leave the cannula in place in the tissue. The cannula insertion system may include a locked configuration and an unlocked configuration. In the locked configuration, the cannula may be locked to the cannula inserter so that there is minimal motion between components. In the unlocked configuration, the cannula may be allowed to disengage from the cannula inserter. In the unlocked configuration, a dilator component 114 of the cannula inserter may be allowed to slide relative to remaining components of the cannula inserter along a central axis of the cannula inserter.

Referring to FIGS. 14 and 17-19, the cannula inserter 100 may include a handle 110, a knob 112, a dilator 114, a first pin 122, a second pin 126, and a spring 140.

Figure 18:
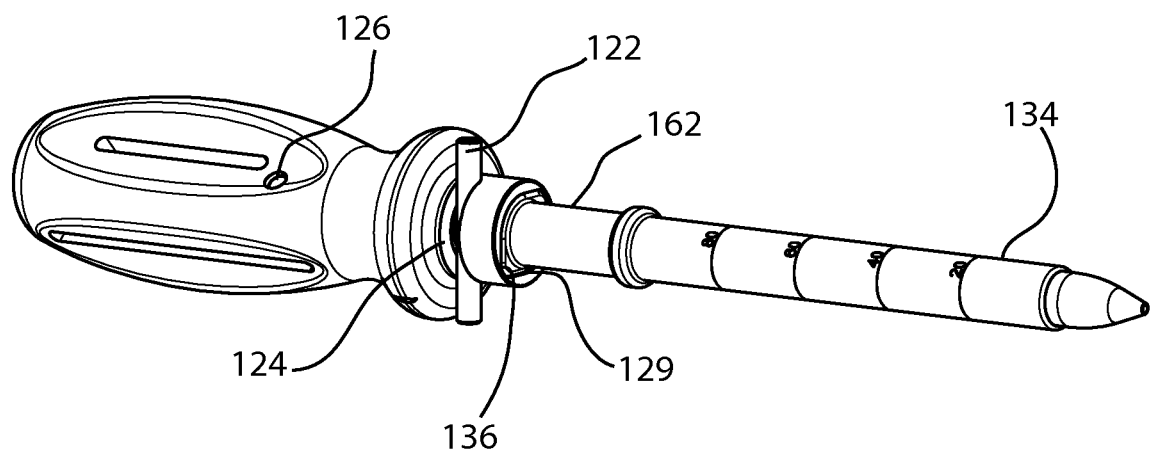
FIG. 18 is a side perspective view of the cannula inserter and cannula of FIG. 9 in the locked configuration, with a knob of the cannula inserter hidden.
Figure 21:
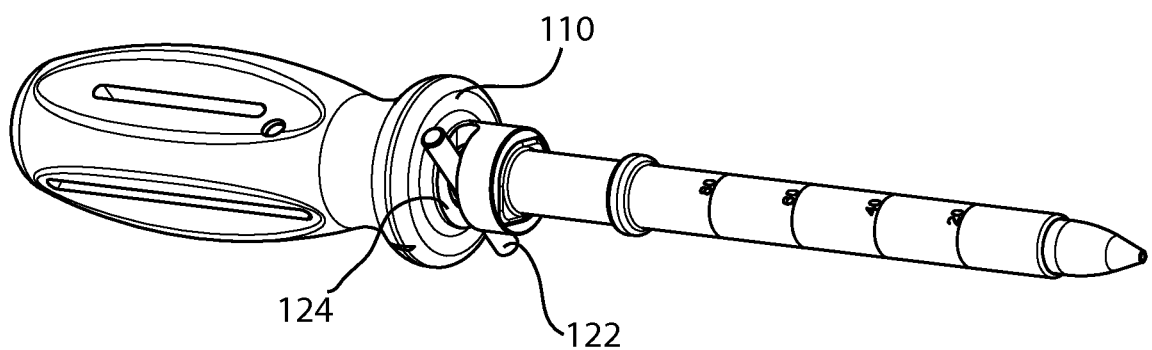
FIG. 21 is a side perspective view of the cannula inserter and cannula of FIG. 9 in the unlocked configuration, with the knob of the cannula inserter hidden.
Figure 26:
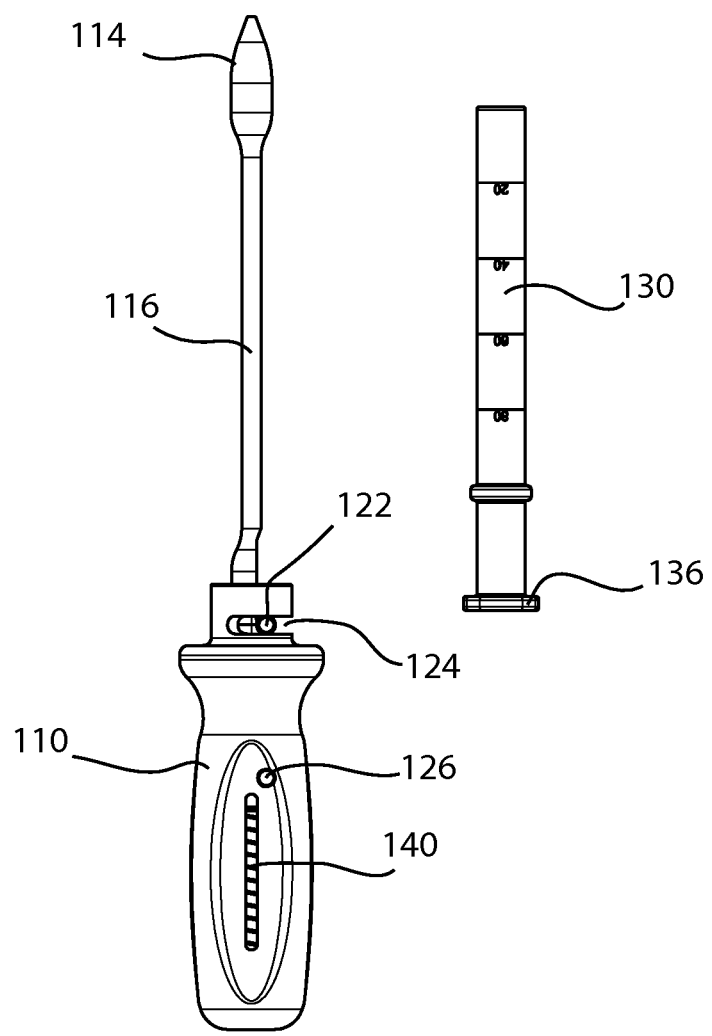
FIG. 26 is a side view of the cannula inserter and cannula of FIG. 21 in the unlocked configuration, with the knob hidden and the cannula alongside the cannula inserter.

Referring to FIGS. 18, 21, and 26, the handle 110 may be an elongated part extending between a distal portion 152 and a proximal portion 154. The handle may include a capture feature 124 (FIG. 18). The capture feature may be a slot which receives the first pin 122. The slot may be shaped or sized so there is interference on the first pin 122 when the first pin is between the locked and unlocked configurations. For example, the majority of the capture feature may be equal to or narrower than the outer diameter of the first pin. The capture feature may include one or more enlarged portions which are equal to or wider than the outer diameter of the first pin. The enlarged portions may coincide with functional positions of the first pin in the capture feature. The handle may also include a keyway 129, which may be located in the distal portion. The handle may be cannulated along its length.

Referring to FIGS. 11-12 and 15-16, the knob 112 may be a generally cylindrical part extending between a distal portion 156 and a proximal portion 157. The knob may include a central aperture 120. The aperture may be circular or non-circular, and may extend through the entire knob. The illustrated aperture 120 is generally circular and is enlarged in one direction by opposing alcoves or keyways. In some examples, the knob or the aperture may include additional engagement features characteristic of a quick connect, quarter turn connection, tongue and groove connection, or bayonet connection. In other examples, the aperture may be threaded or tapered. In yet other examples, the aperture may include a releasable snap connection or collet. The knob may be cannulated along its length.

Figure 25:
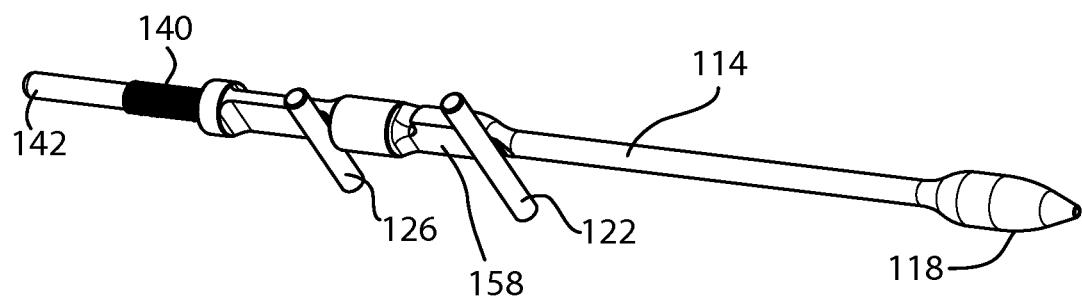
FIG. 25 is a side perspective view of the cannula inserter and cannula of FIG. 9 in the unlocked configuration with the dilator retracted, with the knob and handle of the cannula inserter hidden.

Referring to FIGS. 14, 19, 22 and 25, the dilator 114 may be an elongated part extending between a proximal portion 142 and a distal portion 118 (FIG. 25). The distal portion may be described as a tip 118. The dilator may include a shaft 116 extending between the proximal and distal portions. The shaft may be smaller in diameter than the proximal or distal portions. The dilator may also include a groove 128 which receives the first pin 122. The groove may be adjacent to a flat 158. The groove and the flat may form an angle, which may be obtuse, right, or acute. The dilator may include another flat 160 which may be proximal to the flat 158. The dilator may be cannulated along its length.

Figure 15:
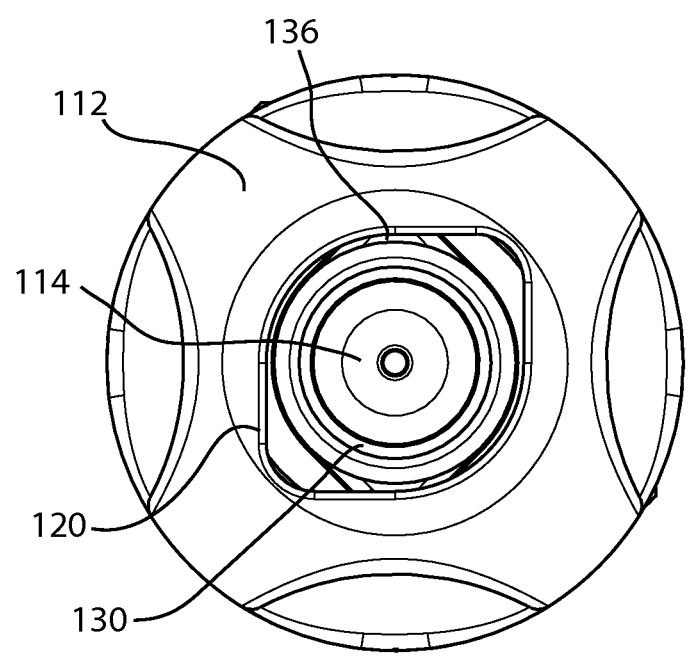
FIG. 15 is an end view of the cannula inserter and cannula of FIG. 9 in the locked configuration.
Figure 16:
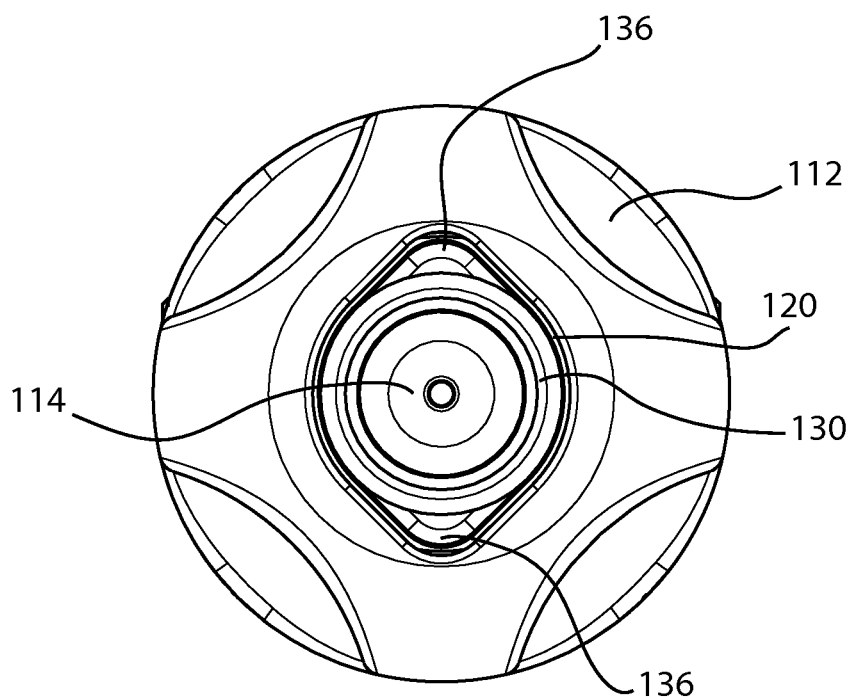
FIG. 16 is an end view of the cannula inserter and cannula of FIG. 9 in the unlocked configuration.

Referring to FIGS. 15-16 and 18, the cannula 130 may be an elongated tubular part extending between a distal portion 134 and a proximal portion 162. The cannula may include a central bore 132 along its length. An engagement feature 136 may be present on the proximal portion. The engagement feature may include at least one protrusion. In the illustrated example, the engagement feature includes two opposing protrusions, or tabs. The engagement feature may be complementary to the knob aperture 120, any additional engagement features of the knob that may be present, and/or the handle keyway 129. The cannula may include depth marks or other indicia or markings.

Figure 17:
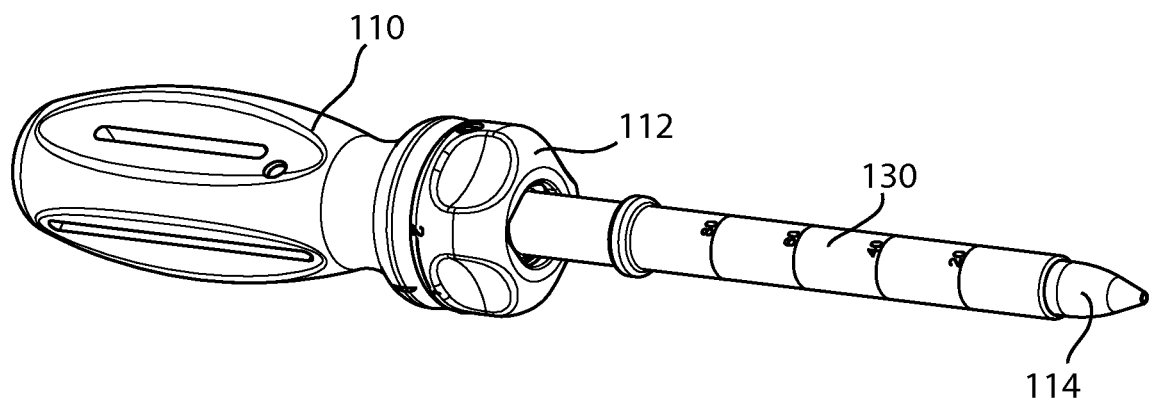
FIG. 17 is a side perspective view of the cannula inserter and cannula of FIG. 9 in the locked configuration.
Figure 19:
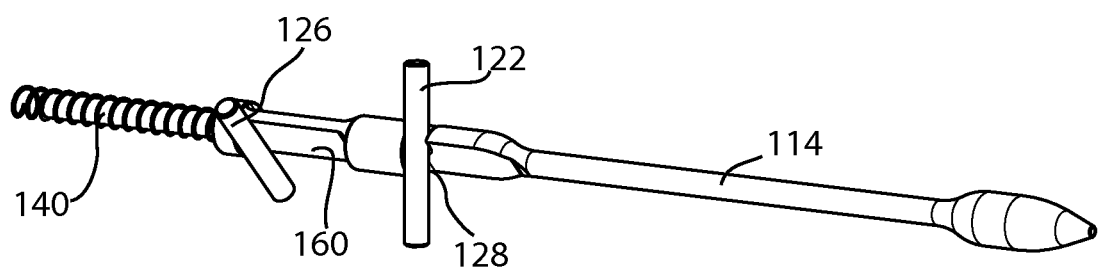
FIG. 19 is a side perspective view of the cannula inserter and cannula of FIG. 9 in the locked configuration, with the knob and a handle of the cannula inserter hidden.
Figure 20:
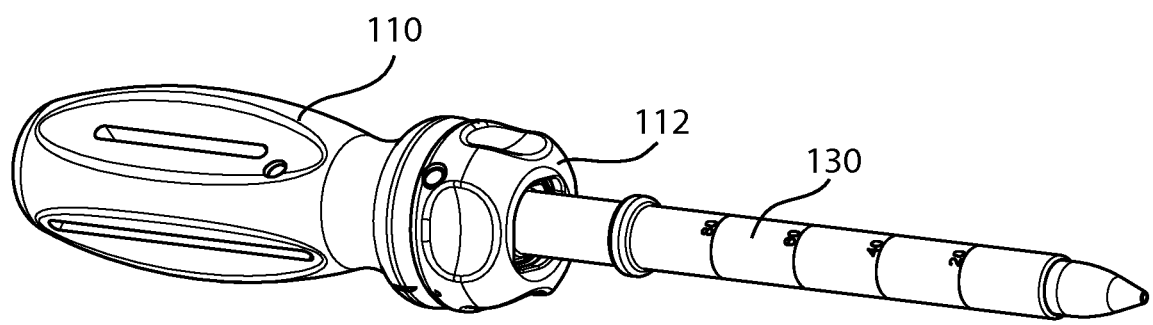
FIG. 20 is a side perspective view of the cannula inserter and cannula of FIG. 9 in the unlocked configuration.
Figure 22:
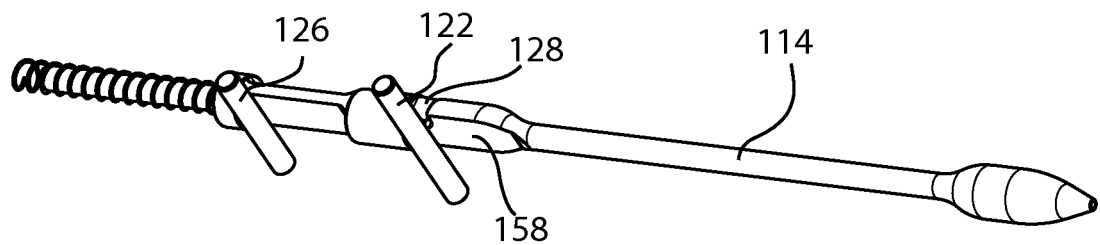
FIG. 22 is a side perspective view of the cannula inserter and cannula of FIG. 9 in the unlocked configuration, with the knob and handle of the cannula inserter hidden.

The cannula inserter 100 may be assembled by sliding the knob proximal portion 157 onto the handle distal portion 152 and sliding the spring 140 and the dilator proximal portion 142 into the handle distal portion. The dilator may be coupled to the handle by the second pin 126 so that the dilator is rotationally fixed relative to the handle and axially slidable relative to the handle, at least within a limited range of axial motion. In FIGS. 19 and 25, the second pin is shown adjacent to the flat 160, an arrangement that may provide the rotational and axial constraints between the dilator and handle. The spring may bias the dilator to one end of the range of axial motion. For example, the spring may be compressed between the handle and the dilator so that the spring urges the dilator to protrude distally from the handle. The knob may be coupled to the handle by the first pin 122 so that the knob is axially fixed relative to the handle and rotatable relative to the handle, at least within a limited range of rotational motion. In FIGS. 17-22, the first pin is shown inserted through the knob so that the first pin is received in the handle capture feature 124, an arrangement that may provide the rotational and axial constraints between the knob and the handle. The first pin may also engage the dilator groove 128 so that rotation of the knob selectively prevents or allows the dilator to slide axially relative to the handle. In FIGS. 17-19, the first pin is shown in dilator groove 128 when the knob is rotated to a first position, which may be a locked position. In FIGS. 20-22, the first pin is shown adjacent to the flat 158 when the knob is rotated to a second position, which may be an unlocked position. The handle and/or knob may include markings or other indicia to show when the knob is in the locked position or the unlocked position.

Figure 10:
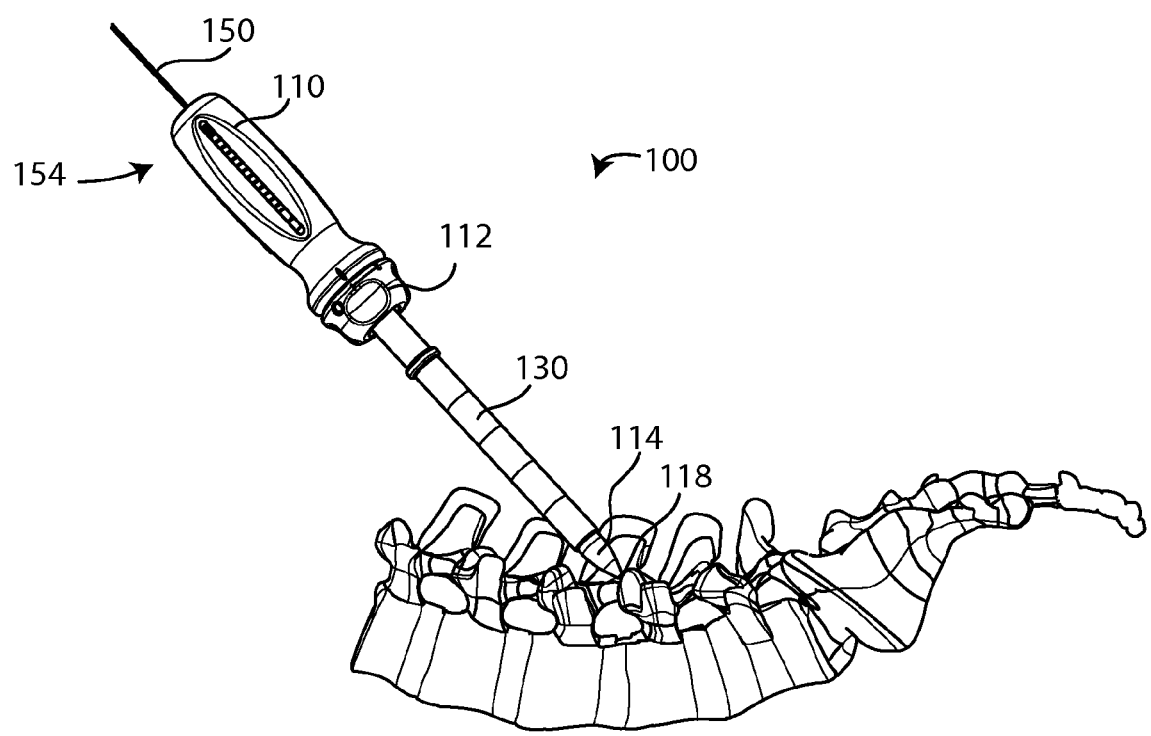
FIG. 10 is a lateral view of the lumbar spine, guide wire, cannula inserter, and cannula of FIG. 9, illustrating a surgical step in which the cannula inserter, with attached cannula, has been advanced to a target location.

The cannula inserter 100 and cannula 130 may be assembled by rotating the knob 112 to the unlocked position, sliding the dilator tip 118 into the proximal portion 162 of the cannula bore 132, aligning the cannula engagement feature 136 with the knob aperture 120, sliding the cannula engagement feature into the knob aperture, and rotating the knob to the locked position. FIG. 10 illustrates that the cannula engagement feature may also fit into the handle keyway 129. In this example, the cannula is rotationally fixed to the handle by the complementary noncircular shapes of the cannula engagement feature and the handle keyway, while the cannula is axially a fixed to the cannula inserter by the misalignment of the knob aperture and the cannula engagement feature when the knob is in the locked position.

Figure 11:
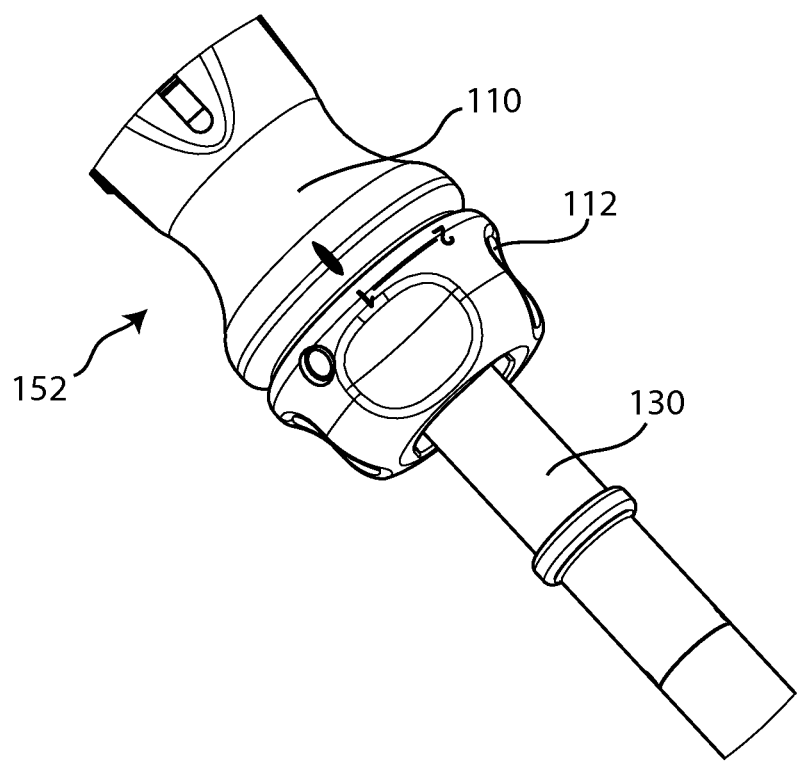
FIG. 11 is an enlarged detail view of a portion of the cannula inserter and cannula of FIG. 9 in a locked configuration.

Referring to FIG. 11, knob 112 is shown in the first or locked position, in which the instrument is in the locked configuration. In this configuration, the instrument handle 110 and knob 112 are in a fixed position relative to the shaft 116 and dilator 114, and the cannula 130 is also in a fixed position relative to the cannula inserter 100.

Figure 12:
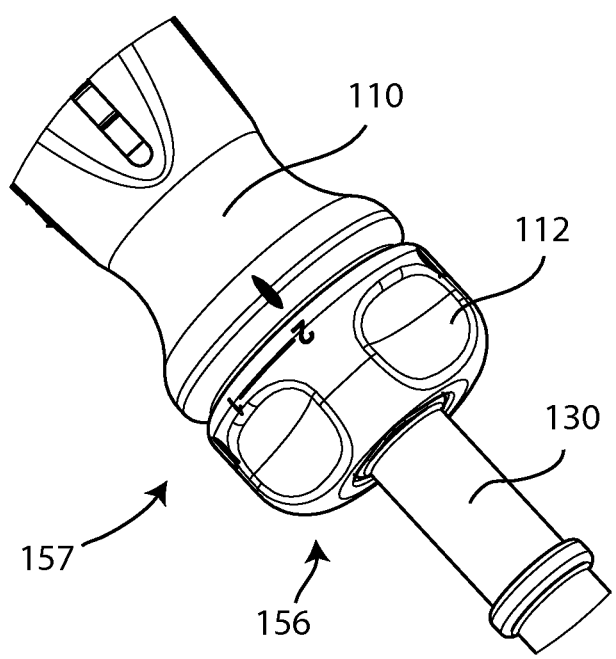
FIG. 12 is an enlarged detail view of a portion of the cannula inserter and cannula of FIG. 9 in an unlocked configuration.

Referring to FIG. 12, knob 112 is shown rotated to the second or unlocked position, which changes the instrument from the locked configuration to the unlocked configuration.

FIGS. 15 and 16 are distal end views of cannula inserter 100, showing the concentric arrangement of the knob 112, cannula 130, and dilator 114. Referring to FIG. 15, knob 112 is in the first, or locked position. In this position, the knob aperture 120 is positioned relative to the cannula engagement feature 136 such that the cannula engagement feature 136 is prevented from moving through the aperture 120. In this configuration, the cannula 130 is locked into engagement with the cannula inserter 100.

Referring to FIG. 16, knob 112 is in the second, or unlocked position. In the position, the cannula engagement feature 136, which in this embodiment comprises at least one protrusion, is aligned with the knob aperture, and the cannula may be disengaged from the instrument.

FIGS. 17, 18, and 19 show various views of the cannula inserter 100 in the locked configuration. FIG. 18 has the knob 112 removed to show how the first pin 122 rests in the capture feature 124 of the handle; in this embodiment the capture feature is an undercut or a slot. It also shows how the cannula 130 is keyed to the end of the handle 110, as engagement feature 136 is captive in the keyway 129. FIG. 19 has the cannula and handle removed to show the first pin 122 and the second pin 126. The first or distal pin 122 rests in the groove 128 on the dilator 114 and prevents the dilator from sliding along the central axis relative to the rest of the instrument, while in the locked configuration. The second or proximal pin 126 prevents rotation of the dilator 114 with respect to the handle 110.

FIGS. 20, 21, and 22 show the same three views shown previously, only in the unlocked configuration. When the knob is turned, the first or distal pin 122 moves in the capture feature 124 on the end of the handle 110 (FIG. 21). This capture feature may be a slot shaped so there is interference, or drag, on the pin 122 when the pin 122 is between configurations. The pin 122 snaps into position when in either configuration. FIG. 22 shows the first pin 122 rotated out of the groove 128 on the dilator 114 allowing the dilator to slide along the central axis relative to the rest of the instrument.

Figure 23:
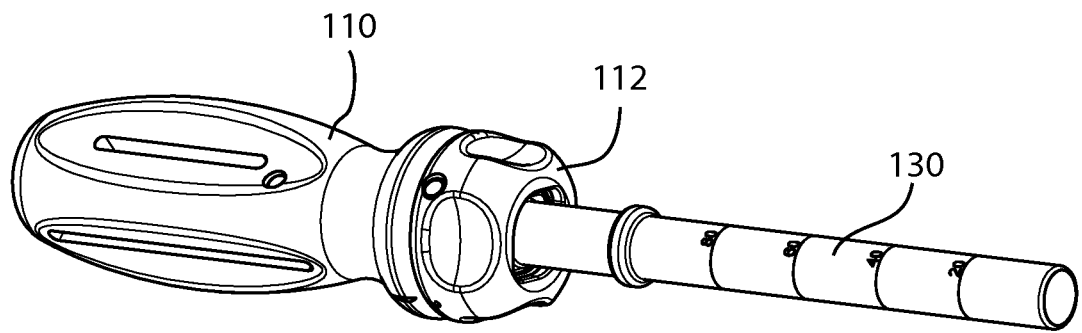
FIG. 23 is a side perspective view of the cannula inserter and cannula of FIG. 9 in the unlocked configuration with a dilator portion of the cannula inserter in a retracted position.
Figure 24:
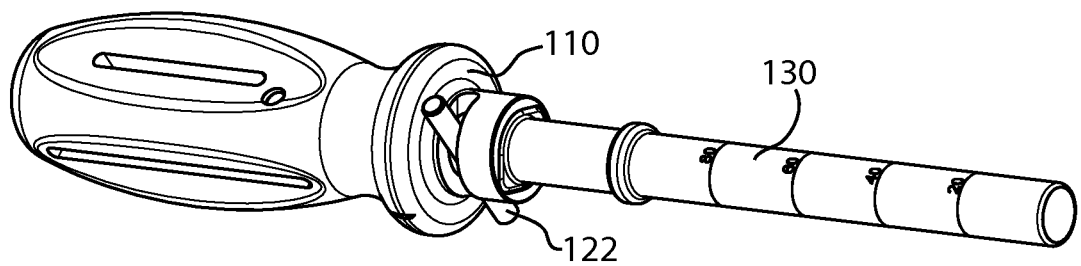
FIG. 24 is a side perspective view of the cannula inserter and cannula of FIG. 9 in the unlocked configuration with the dilator retracted, with the knob of the cannula inserter hidden.

FIGS. 23, 24 and 25 show the same three views shown previously, only in an unlocked configuration with the dilator slid proximally so that a portion is retracted into the rest of the instrument. FIG. 25 shows that the spring 140 is compressed as the dilator 114 slides in, or proximally. The spring 140 presses between the handle 110 and the dilator 114 and keeps the dilator slid out, or distally, when no outside forces are acting on the instrument (FIG. 22). Also, the proximal end 142 of the dilator 114 may exit the handle 110 when the dilator is retracted and thus may act as an indicator that the dilator has slid in.

FIG. 26 displays cannula inserter 100 minus knob 112, in the unlocked configuration. Cannula 130 is shown alongside the cannula inserter.

The cannula inserter 100 and/or cannula 130 may be formed of molded parts, and may be suitable for single use. Alternatively, the cannula inserter, or selected components thereof, or the cannula may be formed of metal, glass, polymer, ceramic, wood, composite materials, or other materials. Any component may be formed of a combination of materials, the material in each portion selected according to the function and working load of the portion.

In one method of use, screw system 10 may be implanted across a facet joint to provide joint fixation, preventing articulation of the joint. A guide wire may be inserted across the joint, and a cannula inserted over the guide wire to the proximal facet. A cannula insertion system providing tissue dilation and cannula insertion, such as that disclosed herein and in U.S. Provisional Patent Application No. 61/374862, incorporated by reference into this disclosure, may be used to insert the cannula. The cannula may be temporarily docked to the proximal facet.

Figure 9:
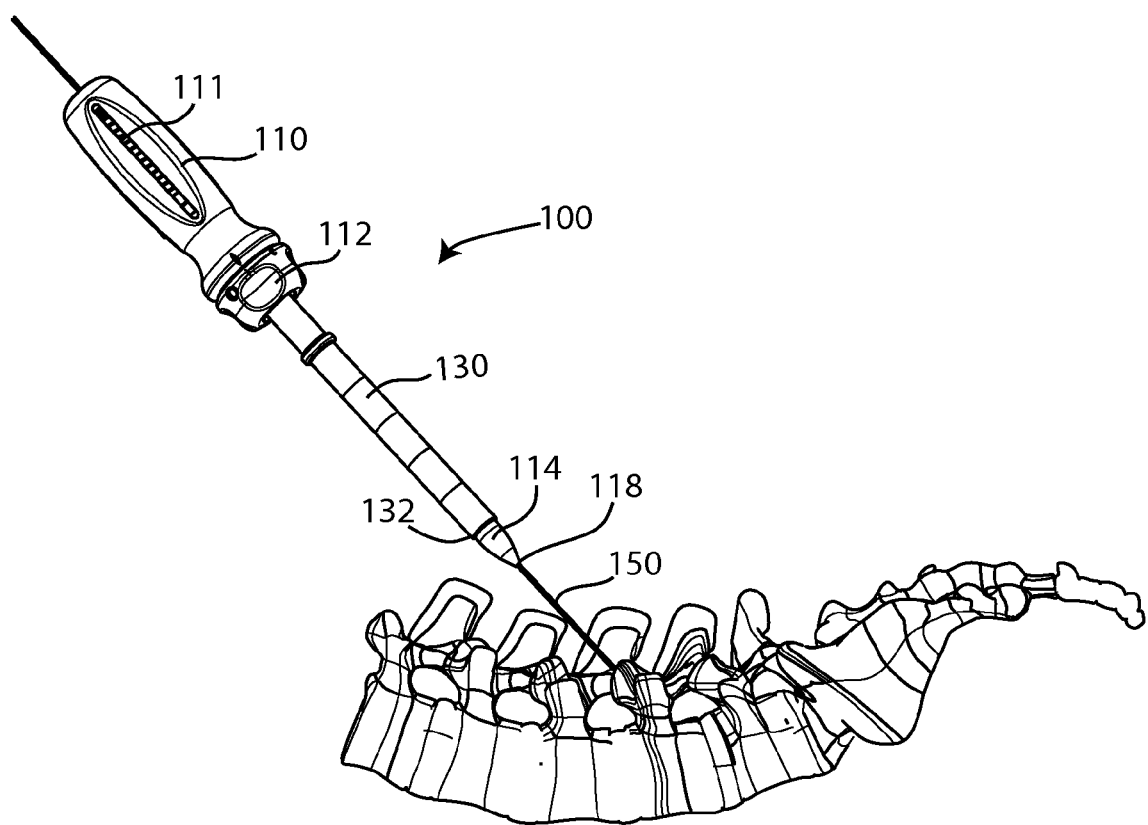
FIG. 9 is a lateral view illustrating a surgical step in which a tip of a guide wire has been inserted across a facet joint of a lumbar portion of a spine, and a cannula inserter, with attached cannula, has been passed over the guide wire.

Referring to FIG. 9, a guide wire 150 may be inserted across a facet joint to establish an insertion trajectory for screw system 10. The illustrated trajectory is generally postero-cephalad to antero-caudal. The guide wire is shown deeply inserted within an inferior pedicle associated with the facet joint.

The cannula inserter 100 and cannula 130 may be assembled and set to the locked configuration as described above. Cannula inserter 100 and cannula 130 may be started over the guide wire 150 and moved through intervening soft tissue toward a target location while in the locked configuration. In this example, the target location is a facet joint in a spine. More specifically, the illustrated target location is a location on an inferior articular process of the facet joint. Cannula 130 is releasably locked to the cannula inserter 100 and extends longitudinally along the shaft 116 of the instrument, such that the bore 132 of the cannula 130 surrounds the shaft 116 and the dilator 114 protrudes from the cannula bore 132.

Referring to FIG. 10, cannula inserter 100 has been moved through the soft tissue and the distal tip 118 of dilator 114 is at the target location. However, the distal portion 134 of the cannula 130 remains at a distance from the target location.

Figure 13:
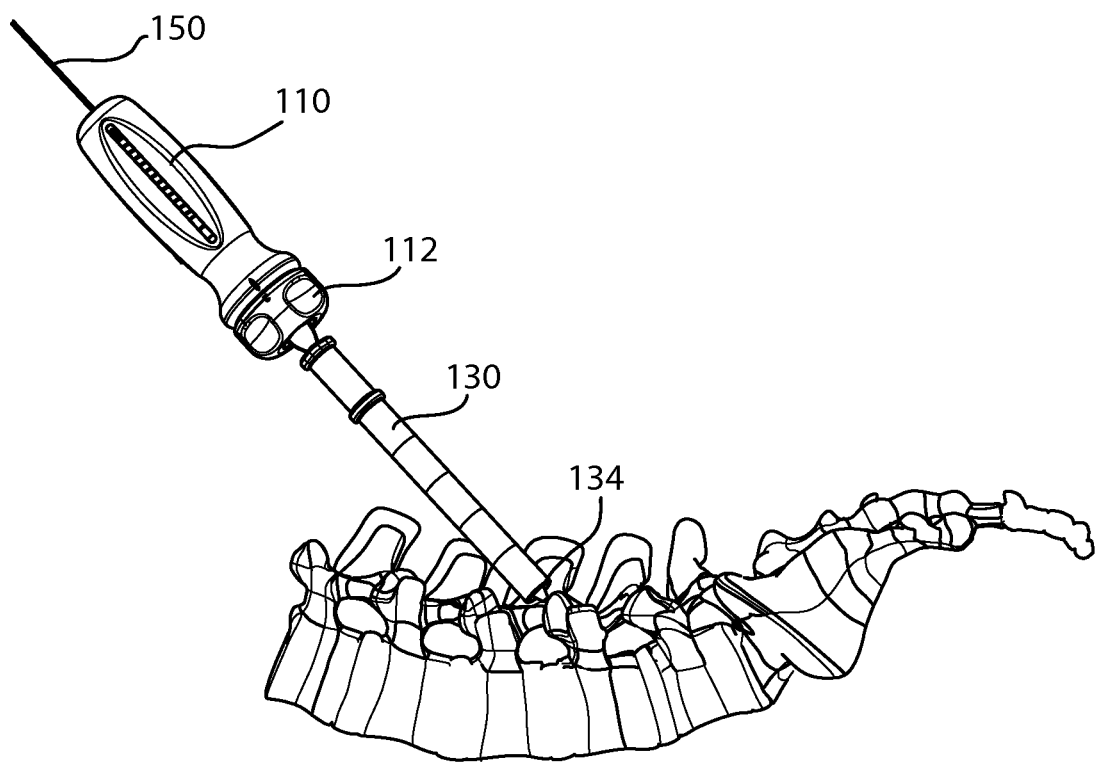
FIG. 13 is a lateral view of the lumbar spine, guide wire, and cannula inserter of FIG. 9, illustrating a surgical step in which the cannula has been advanced to the target location over the dilator.

Referring to FIG. 13, the cannula inserter 100 has been set to the unlocked configuration. The handle 110, knob 112 and cannula 130 have moved toward the target location, translating along the dilator shaft 116 toward the tip 118. As the cannula 130 moves distally along the shaft, dilator 114 is received in the bore 132 of the cannula 130. A distal end 134 of the cannula may directly contact the target location, which may be a bone. In the example shown, the target location is an inferior facet. The dilator tip 118 may push against the target location as the cannula 130, handle 110 and knob 112 translate relative to the shaft 116.

Figure 14:
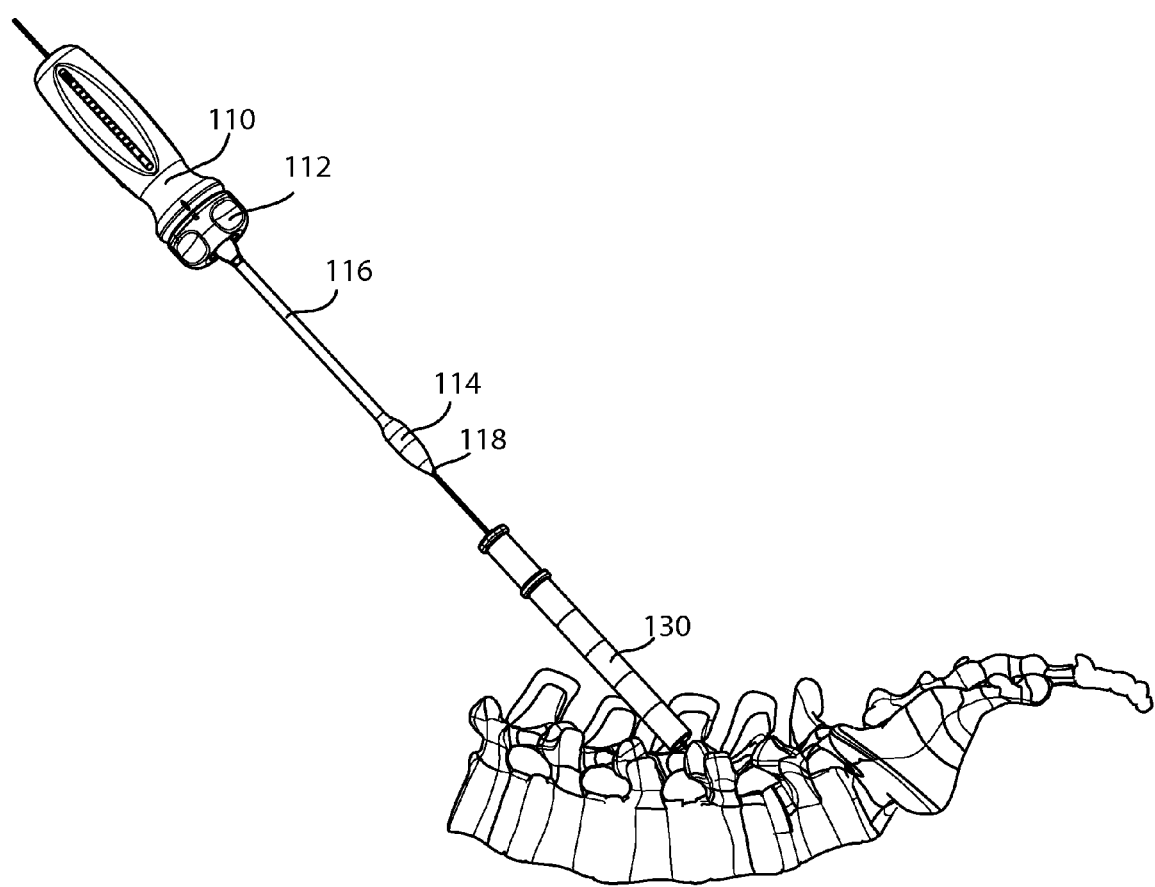
FIG. 14 is a lateral view of the lumbar spine, guide wire, and cannula inserter of FIG. 9, illustrating a surgical step in which the cannula inserter has been withdrawn from the cannula, which remains at the target location.

Referring to FIG. 14, the unlocked cannula inserter 100 has been withdrawn proximally along the guide wire 150, leaving cannula 130 in situ at the target location.

The operatively assembled screw system 10 may be inserted through the cannula 130 to the facet joint, with the screw first end 34 leading. A driver is used to rotate screw 20 in the first direction 90, driving screw 20 through the facets and across the joint. As screw 20 is driven, washer 42 comes in contact with the proximal facet, with at least a portion of bone engagement surface 68 in contact with the bony material of the facet. The polyaxial adjustability of the washer assembly relative to the screw allows the washer to sit at an angled position relative to the screw, which may be dictated by the surface topography of the facet and/or the surrounding environment. As screw 20 is driven further, spikes 69 may penetrate the surface of the facet, providing enhanced fixation and anti-rotation. When desired fixation of the joint and compression of the washer against the facet is achieved, rotation of screw 20 is ceased. Unintentional back-out and/or unintentional loosening of screw system 10 is prevented, as any rotation of screw 20 in second direction 92 results in locking together of screw 20 and washer assembly 40. Since washer assembly 40 is stabilized against the facet by spikes 69, screw 20 is effectively prevented from backing out or loosening.

Screw system 10 may be used in other applications in which two bone segments are fixed or compressed together to provide fixation or arthrodesis of a joint. The system may also be used in any orthopedic application in which anti-backout capabilities are desired, for example, to attach a prosthesis or implant to a bone. Non-limiting examples include attachment of articulating facet joint prostheses to vertebrae, attachment of intervertebral disk replacement prostheses, attachment of spinal rods, attachment of bone plates, and attachment of other joint prostheses, including knee, hip, shoulder, wrist, and/or ankle prostheses. Screw system 10 may also provide an anchor for anchoring of sutures, or natural or artificial tissues such as muscle, tendon, or ligament. One of skill in the art may appreciate that washer assembly 40, for example, may be modified by replacing washer 42 with an alternate component, which may include some or all of the features described above for washer 42.

The components of system 10 are preferably formed of titanium or titanium alloy. In other embodiments, system 10 or any of its component parts may comprise cobalt-chrome and its alloys, stainless-steel, titanium and its alloys, titanium carbide, titanium nitride, ion-implantation of titanium, diffusion hardened metals, diamond like coatings, diamond-like carbon, zirconium nitride, niobium, oxinium or oxidized zirconium, ceramics such as alumina and zirconia, polymers, or other biocompatible materials. Any part may comprise a combination of any of the materials listed, and the system 10 may comprise parts made of differing materials.

In another example of the cannula insertion system, the cannula inserter 100 may include a plurality of dilators 114 of varying or graduated diameters. This plurality of intermediate dilators may be positioned between an initial or smallest dilator and the final cannula 130. The knob 112 may include intermediate positions that selectively free up or unlock the intermediate dilators to slide into the handle. In another example, the spring 140 may be omitted from the assembly. In another example, the cannula inserter 100 may include a ratchet system to retract the dilator. In another example, the cannula inserter 100 and cannula 130 may be used without a guide wire. Another example may include other locking connections between the cannula and the instrument, such as a releasable snap fit, a threaded connection, a tongue and groove connection, a tab or button and slot connection, among other locking connections.

Any of the components disclosed herein may include surface treatments or additives in one or more of the component materials to provide beneficial effects such as anti-microbial, analgesic or anti-inflammatory properties. Any of the components disclosed herein may include coatings or treatments to provide surface roughening, including but not limited to knurling or porous coating, among others. Such treatments may be directionally applied to promote movement between component parts in one direction, and/or increase friction between component parts in another direction.

The present subject matter may be embodied in other specific forms without departing from its spirit or essential characteristics. It is appreciated that various features of the above described examples and embodiments may be mixed and matched to form a variety of other combinations and alternatives. It is also appreciated that this system should not be limited simply to facet joint fixation. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system, comprising:
   a handle;
   a dilator coupled to the handle;
   a tubular cannula removably coupled to the handle;
   a selector having a first pin coupled to the dilator; and a second pin coupled to the dilator, said second pin adapted to provide rotational and axial motion constraints for the system;

wherein the system is transformable between a first setting and a second setting by rotating the first pin into or out of engagement with a groove of the dilator;

wherein, in the first setting, the dilator is fixed to the handle in an extended position in which a first length of the dilator protrudes from the handle and the cannula is fixed to the handle so that a length of the cannula protrudes from the handle and the dilator extends through the cannula less than the first length of the dilator;

wherein, in the second setting, the dilator is slidable relative to the handle between the extended position and a retracted position in which a second length of the dilator protrudes from the handle, the second length being less than the first length and the cannula being removable from the handle, wherein the dilator is biased toward the extended position to temporarily overcome the retracted position, wherein the dilator comprises the groove and a flat; wherein, in the first setting, the first pin engages the groove to fix the dilator to the handle; wherein, in the second setting, the first pin engages the flat to permit the dilator to slide relative to the handle between the extended position and the retracted position, wherein the dilator is rotationally fixed to the handle in the extended and retracted positions.

2. The system of claim 1, comprising:

a center longitudinal axis;

wherein the handle and the dilator are aligned with the axis;

wherein the system transforms between the first and second settings in response to rotation of the selector about the axis.

3. A system, comprising:

a cannula comprising a proximal segment, a distal segment, and a central longitudinal hole, wherein the distal segment is opposite the proximal segment, wherein the central longitudinal hole extends through the proximal and distal segments; and an instrument comprising a dilator, the dilator comprising a distal portion, said instrument further comprising a first pin and a second pin coupled to the dilator, said second pin adapted to provide rotational and axial motion constraints for the system;

wherein the system is transformable between a first setting and a second setting by rotating the first pin into or out of engagement with a groove of the dilator;

wherein, in the first setting, the cannula proximal segment is fixed to the instrument and the dilator is fixed to the instrument in an extended position in which a first length of the dilator protrudes from the instrument, at least a portion of the dilator is inside the cannula hole, and the dilator distal portion protrudes at least partially from the cannula distal segment;

wherein, in the second setting, the dilator is slidable relative to the instrument between the extended position and a retracted position in which a second length of the dilator protrudes from the instrument, the cannula is slidable relative to the instrument, and the dilator is slidable relative to the cannula, the second length being less than the first length and the cannula being removable from the instrument, wherein the dilator comprises the groove and a flat, wherein, in the first setting, the first pin engages the groove to fix the dilator to the instrument, wherein, in the second setting, the first pin engages the flat to permit the dilator to slide relative to the instrument, wherein the dilator is rotationally fixed to the instrument in the extended and retracted positions.

4. The system of claim 3, wherein, in the second setting, the dilator is slidable relative to the instrument between a distal position and a proximal position; wherein, in the distal position, a first distal position length of the dilator protrudes from the instrument; wherein, in the proximal position, a second proximal position length of the dilator protrudes from the instrument, wherein the second proximal position length is less than the first distal position length.

5. The system of claim 4, wherein the dilator is biased toward the distal position; wherein, in the second setting, sliding the dilator toward the proximal position temporarily overcomes the bias.

* * * * *